United States Patent
Wool

(10) Patent No.: US 10,143,539 B2
(45) Date of Patent: Dec. 4, 2018

(54) CRIMP STOP AND METHOD OF MAKING THE SAME

(71) Applicant: Modern Arch, LLC, Wyomissing, PA (US)

(72) Inventor: Arthur L. Wool, Wyomissing, PA (US)

(73) Assignee: MODERN ARCH, LLC, Wyomissing, PA (US)

( * ) Notice: Subject to any disclaimer, the term of this patent is extended or adjusted under 35 U.S.C. 154(b) by 0 days.

(21) Appl. No.: 15/429,800

(22) Filed: Feb. 10, 2017

(65) Prior Publication Data

US 2017/0215994 A1    Aug. 3, 2017

Related U.S. Application Data

(62) Division of application No. 12/169,717, filed on Jul. 9, 2008, now abandoned.

(60) Provisional application No. 60/948,558, filed on Jul. 9, 2007.

(51) Int. Cl.
| | |
|---|---|
| *A61C 7/26* | (2006.01) |
| *A61C 7/12* | (2006.01) |
| *A61C 7/00* | (2006.01) |
| *A61C 7/28* | (2006.01) |

(52) U.S. Cl.
CPC .................. *A61C 7/12* (2013.01); *A61C 7/00* (2013.01); *A61C 7/28* (2013.01); *Y10T 29/49568* (2015.01)

(58) Field of Classification Search
CPC ........................................................ A61C 7/12
See application file for complete search history.

(56) References Cited

U.S. PATENT DOCUMENTS

| | | | |
|---|---|---|---|
| 2,993,980 | A | 7/1961 | Dunn |
| 3,508,332 | A | 4/1970 | Armstrong |
| 3,827,815 | A | 8/1974 | Strange |
| 4,226,550 | A | 10/1980 | Kupcak |
| 4,627,144 | A | 12/1986 | Burke |
| 4,639,219 | A | 1/1987 | Gagin |
| 4,717,341 | A | 1/1988 | Goldberg |
| 4,844,066 | A | 7/1989 | Stein |
| 5,306,142 | A | 4/1994 | Richards |
| 6,558,160 | B2 | 5/2003 | Schnaitter |
| 7,033,170 | B2 | 4/2006 | Cordato |
| 2006/0228664 | A1 | 10/2006 | Castner |
| 2007/0042314 | A1 | 2/2007 | Brosius |

*Primary Examiner* — Ryan J Walters
(74) *Attorney, Agent, or Firm* — Fitch, Even, Tabin & Flannery, LLP

(57) ABSTRACT

A crimp stop is made of a metal formed member having a U-shaped cross-section. The metal formed member has a size and shape configured to receive an orthodontic archwire into the U-shaped cross-section and configured to be crimped onto the orthodontic archwire so as to maintain position of the metal formed member after being crimped on the orthodontic archwire by friction. The metal formed member has a curved portion and a pair of legs attached to the curved portion; the legs are not parallel to each other and diverge at an angle.

8 Claims, 1 Drawing Sheet

CRIMP STOP AND METHOD OF MAKING THE SAME

CROSS-REFERENCE TO RELATED APPLICATION

This application is a divisional application of application Ser. No. 12/169,717, filed Jul. 9, 2008, which is a nonprovisional application claiming benefit of the filing date of provisional application Ser. No. 60/948,558, filed Jul. 9, 2007, the contents of each of which are incorporated herein in their entireties.

BACKGROUND OF THE INVENTION

Prior art crimp stops are cast from melted steel or are injection molded and are very thick in dimension. A thicker crimp stop that is annealed by melting can be adequately soft, but have the drawbacks of being bulky and expensive, as more metal is squeezed against the underlying wires.

One prior art crimp stop is disclosed by Brosius, US PG Pub 2007/0042314 A1, which provides a crimpable orthodontic device attempting to solve the problem of crimp stops tending to slide down an archwire. As stated by Brosius, methods such as coating the inner side of the stop has drawbacks including cost and also the coating may wear off over time. In Brosius ('314), the inner surfaces of the crimp stop are etched, stamped, or otherwise roughened to increase friction and resist slippage between the crimpable stop and the orthodontic wire. The prior art device of Brosius ('314) also includes upper and lower edges to lock around the archwire to hold the wire in place. Brosius ('314) involves an etching process to increase the holding power, but the full annealing of thin-walled, non-cast or non-molded crimp stops to greatly improve their working and holding power is not disclosed. The prior art does not teach or disclose fully annealing the stainless steel crimp stop to soften the stop and allow it to be crimped in place.

SUMMARY OF THE INVENTION

The present invention relates to a crimp stop comprising a U-shaped cross-section member made of a metal material. The metal formed member has a size and shape configured to receive an orthodontic archwire into the U-shaped cross-section and configured to be crimped onto the orthodontic archwire so as to maintain position of the metal formed member after being crimped on the orthodontic archwire by friction. The metal formed member has a curved portion and a pair of legs attached to the curved portion; the legs are not parallel to each other and diverge at an angle.

The member can be annealed to soften the metal material.

The present invention also relates to a process for making a crimp stop, comprising forming a metal material into a member having a U-shaped cross-section, and annealing the member by heating, and cooling the annealed member to soften the metal material.

BRIEF DESCRIPTION OF THE SEVERAL VIEWS OF DRAWINGS

DETAILED DESCRIPTION OF THE INVENTION

Figure 2:
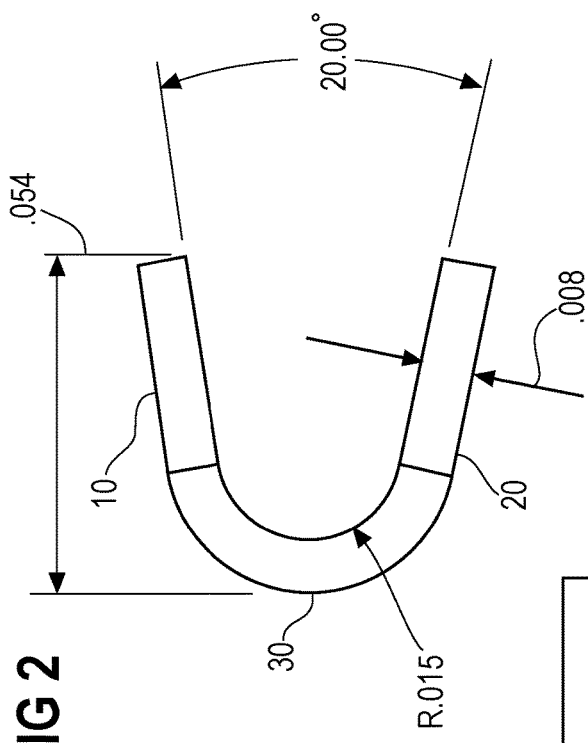
FIG. 2 is a side view of a crimp stop of the present invention.

This invention relates to an improved orthodontic device and method of making the same. More particularly, this invention relates to a method of making a crimp stop in a simpler and more cost effective manner than prior art crimp stops. By fully annealing a crimp stop of a desired thickness, a soft crimp stop may be fastened to an orthodontic wire without costly and time consuming steps such as etching and coating to improve the hold of the crimp stop to the wire.

The crimp stop of the present invention can be made more efficiently, using less steps, and is less costly than the crimp stop now present in the prior art. The present invention uses a simpler method of manufacturing the crimp stop, creating a different product than that of the prior art.

A specially manufactured crimp plier shown in copending application Ser. No. 12/114,924, filed May 5, 2008 by the same inventor (contents of which are incorporated herein in their entireties) is used to crimp the crimp stops onto the wire. As shown in the copending application, the pliers have handles interconnected at pivot and jaws as known in the art. The edges of the pliers are used to squeeze, or crimp, the two walls as shown therein, around an archwire. Two squeezes or crimps are typically needed to fasten the crimp stop to the wire.

Thus, the present invention aims to improve upon the drawbacks of the prior art by fully annealing a crimp stop made of thin stainless steel or equivalent material before or after the stainless steel has been fashioned into a desired U-shape. When prior art crimp stops made of stainless steel are, for example, initially formed and not fully annealed, the material tends to work harden and not produce the level of softness needed to crimp around an orthodontic wire such as an archwire. The present invention corrects this problem by fully annealing the crimp stop, which softens the crimp stop, allowing it to be adequately fastened to the archwire. The crimp stop of the present invention does not require the inner surface of the crimp stop to be roughened, etched or coated in any manner. Thus, by the present invention, a crimp stop is invented that is made in fewer steps than the prior art, and of thinner material, therefore decreasing the time and material cost involved in making a softened crimp stop.

The best mode for carrying out this invention is to use a grade of stainless steel that will retain its shiny silver color during the anneal process. To do this, the crimp stops must be fully annealed in a vacuum chamber or in an inert gas atmosphere (e.g., nitrogen or argon), free of oxygen, so that iron or other metal oxide will not form on the surface of the crimp stops, blackening their color and producing an additional external layer. However, crimp stops of other colors such as black may be used. These are made by annealing the stops in the presence of oxygen. This process may include an extra step of tumbling the crimp stops to remove the loose scale from oxidation, or black dust, which forms when the shiny silver stainless steel becomes black in color. The oxidized black crimp stops function identically to the shiny silver stops.

Whether the crimp stops are shiny silver or jet black, it is the full annealing of the thin material that causes the crimp stop to be adequately soft to be squeezed or crimped onto the archwire. This greatly improves the method of producing the crimp stops of the prior art because the material does not have to be cast or injection molded, which is a more involved and costly process. Also, the inside of the crimp stop need not be coated, etched or roughened in some manner to increase the friction between the crimp stop and the orthodontic wire. Rather, a thin sheet of annealed stainless steel is cut and bent into the desired shape. The desired shape is then fully annealed to the maximum softness of the material to create a softer, thinner crimp stop that is not bulky. The crimp stops crimp and hold very efficiently to an archwire as necessary in orthodontic practices.

Figure 3:
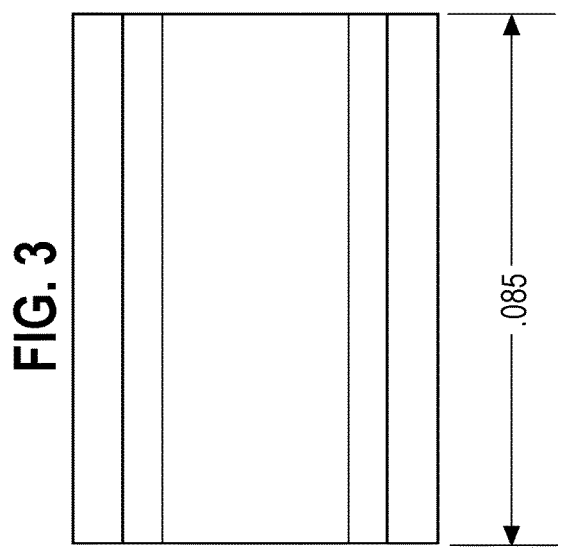
FIG. 3 is a front view of the crimp stop shown in FIG. 2.
Figure 1:
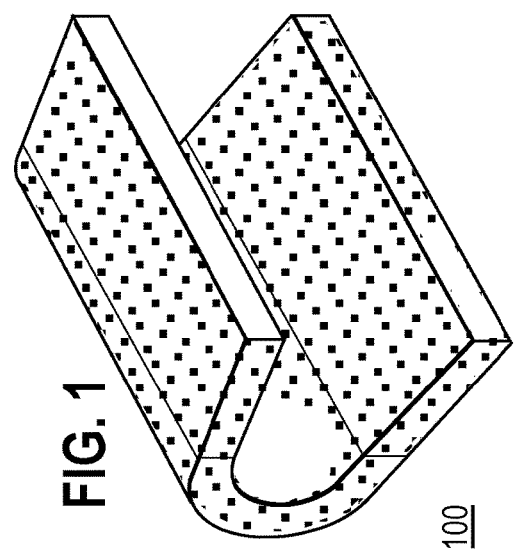
FIG. 1 is a perspective view of a crimp stop of the present invention.

Attention will now be drawn to FIGS. 1-3, and a method of manufacturing the crimp stop of the present invention. A sheet of stainless steel, preferably 304 stainless steel or equivalents, as shown in FIG. 1, is cut and bent into the desired U-shape 100. If not fully annealed after bending into the U-shape, the steel is work hardened at least from the cutting and bending. To remedy this, according to the invention, the U-shape stop 100 is fully annealed after cutting and bending to produce the soft material needed to make the desired crimp stops 100. Equivalents including 302 stainless steel and 316-L stainless steel can also be used. After the crimp stops 100, which are of a uniform thickness, have been shaped into the desired U-shape, they are fully annealed to a desired softness to be able to crimp the stops around a metal archwire. The softness of the crimp stop allows one to crimp, using crimping pliers referenced herein, crimp stops 100 along an archwire in an efficient manner. The crimp stops are adhered to the wire by friction, leaving an indentation on the crimp stops, and a small indentation underneath on the archwire in the same location as the indentation on the crimp stop. Grade 304 stainless steel, for example, must be fully annealed in the temperature range of 1800 to 2100 degrees Fahrenheit, preferably about 1900° F. for about, e.g., 10-20 minutes.

Once the fully annealed stainless steel crimp stop 100 is formed, the stop is able to be crimped onto an archwire or orthodontic wire. The softness of the crimpable stop allows the stop to be crimped onto the wire. This differs from the prior art in that the surface of the inside of the hardened crimp stop need not be roughened, etched, stamped, or otherwise provided with a coating that causes the stop to remain adhered to the wire.

The present invention provides a simple process of forming the crimp stop from very thin and uniform thickness sheet metal that is fully annealed, instead of by casting or molding a relatively thicker stop and etching or coating the metal, provides an adequate softened stop that can be crimped onto and adhered to the archwire by the mutual friction between the stop and the archwire. The dimensions of the crimp stop 100 of the present invention are shown in FIGS. 2 and 3 and are necessarily thinner than the cast crimp stops of the prior art. The crimp stop 100 is preferably between 0.008 to 0.010 inches thick; between 0.50 to 0.60 inches long as shown in FIG. 2; and 0.08 to 0.10 inches wide, as shown from the front view in FIG. 3. Other dimensions could be employed depending on the application and material of construction.

When crimped, the crimp stop 100 of the present invention does not form hooks over the arch wire to maintain position as is characteristic of the prior art. Rather, the end of the U-shaped crimp stop remains open. That is, when the crimpable stop of the present invention is fastened, the two straight edges 10, 20 will lay parallel to each other.

The crimp stop has three sections consisting of two straight legs 10 and 20, and a curved portion 30. When initially formed into a U-shape, before crimping, the legs 10 and 20 are not parallel to each other. Rather, the legs diverge at a small angle, on the order of 15 to 25 degrees, preferably 20 degrees, as shown in FIG. 2. The curved portion 30 is sized large enough to receive the archwire, yet not so large wherein the archwire would have excess room to move around once crimped. When bent, the entire length of the crimp stop is preferably on the order of 0.05 to 0.06 inches, with a radius of curvature on the order of 0.015 inches.

An alternative material to stainless steel is NiCrCo alloy. No iron is included in this alloy. NiCrCo is manufactured under such trade names as MP 35 made by Carpenter Technologies or Elgiloy® made by the Elgin Company. NiCrCo alloy is usually used for arch wires and springs but may also be used for crimp stops. Elgiloy®, for example, will not be work hardened when cutting and bending into the U-shape of the crimp stop, so fully annealing prior to cutting and bending is sufficient for softening the material for use in the crimp stop. No post-bending anneal need be employed. Another alternative material is Nickel-free stainless steel. Some patients are allergic to Nickel against their skin. Therefore, Nickel-free stainless steel may be used as well for a material of the crimp stop.

By use of this simplified process, process steps and added materials can be eliminated, resulting in a crimp stop that can be made more easily and less costly than the crimp stops known to the prior art. The crimp stop of the present invention does not require a further step of etching, roughening or coating to better adhere the thin crimp stop to the archwire as in the prior art crimp stops. Nor is the shape of the crimp stop dependent upon hook shaped edges as disclosed in the prior art crimp stops to overlap the wire for holding the wire in place.

It will be understood that modifications and variations may be effected without departing from the scope of the novel concepts of the present invention.

What is claimed is:

1. A crimp stop comprising a metal formed member having a U-shaped cross-section, the metal formed member having a size and shape configured to receive an orthodontic archwire into the U-shaped cross-section and configured to be crimped onto the orthodontic archwire so as to maintain position of the metal formed member after being crimped on the orthodontic archwire by friction, the metal formed member having the U-shaped cross-section having a curved portion and a pair of straight legs attached to the curved portion and extending to an open end configured to receive the orthodontic archwire, wherein the legs are not parallel to each other and diverge along an entire distance from the curved portion to the open end at an angle of 15-25 degrees, wherein the metal formed member has a thickness of 0.008 to 0.010 inches.

2. The crimp stop according to claim 1, wherein the metal is steel.

3. The crimp stop according to claim 1, wherein the metal is a NiCrCo alloy.

4. The crimp stop according to claim 1, wherein the metal formed member is made by forming a metal material to have a U-shaped cross-section, annealing the entire metal formed member by heating, and cooling the annealed member to soften the metal formed material.

5. The crimp stop according to claim 4, wherein a surface of an inside of the U-shaped member is not roughened, etched, stamped, or provided with a coating.

6. The crimp stop according to claim 4, wherein the member is annealed in a temperature range of 1800 to 2100° F.

7. The crimp stop according to claim 1, wherein a distance from a closed end of the curved portion to an edge of each of the pair of legs at the open end is 0.50 to 0.60 inches.

8. The crimp stop according to claim 1, wherein a distance along the curved portion parallel to the archwire to be received therein is 0.08 to 0.10 inches.

* * * * *